United States Patent
Hershkowitz et al.

(10) Patent No.: US 9,809,506 B2
(45) Date of Patent: Nov. 7, 2017

(54) HYDROCARBON CONVERSION TO ETHYLENE

(71) Applicant: ExxonMobil Chemical Patents Inc., Baytown, TX (US)

(72) Inventors: Frank Hershkowitz, Basking Ridge, NJ (US); Paul F. Keusenkothen, Houston, TX (US); Ian J. Laurenzi, Hampton, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/294,898

(22) Filed: Oct. 17, 2016

(65) Prior Publication Data

US 2017/0036971 A1    Feb. 9, 2017

Related U.S. Application Data (62) Division of application No. 14/942,287, filed on Nov. 16, 2015, now Pat. No. 9,499,457.

(Continued)

(30) Foreign Application Priority Data

Feb. 4, 2015    (EP) .................................... 15153727

(51) Int. Cl.
*G05B 17/00*    (2006.01)
*C07C 2/00*    (2006.01)
(Continued)

(52) U.S. Cl.
CPC .................... *C07C 4/04* (2013.01); *B01J 8/04* (2013.01); *B01J 8/0438* (2013.01); *B01J 8/0496* (2013.01);
(Continued)

(58) Field of Classification Search
CPC . B01J 19/24; B01J 19/2485; B01J 8/04; B01J 8/0438; B01J 8/0496;
(Continued)

(56) References Cited

U.S. PATENT DOCUMENTS 2,319,679 A    5/1943  Hasche et al.
2,629,753 A *  2/1953  Frevel ................... C07C 5/3335
                                           585/634

(Continued)

FOREIGN PATENT DOCUMENTS

| GB | 830574 A | 3/1960 |
|----|----------|--------|
| GB | 1240182  | 7/1971 |
| WO | 2012/099679 | 7/2012 |

OTHER PUBLICATIONS

Naik C B et al: "Modeling high pressure ethane oxidation and pyrolysis", Proceedings of the Combusion Institute, Elsevier, NL, vol. 32, No. 1, Jan. 1, 2009, pp. 437-443.

*Primary Examiner* — William Cheung (57) ABSTRACT

The invention relates to a hydrocarbon conversion process and a reactor configured to carry out the hydrocarbon conversion process. The hydrocarbon conversion process is directed to increasing the overall equilibrium production of ethylene from typical pyrolysis reactions. The hydrocarbon conversion process can be carried out by exposing a hydrocarbon feed to a peak pyrolysis gas temperature in a reaction zone in the range of from 850° C. to 1200° C.

13 Claims, 3 Drawing Sheets

Related U.S. Application Data (60) Provisional application No. 62/093,003, filed on Dec. 17, 2014.

(51) Int. Cl.

| | | |
|---|---|---|
| *C07C 4/02* | (2006.01) | |
| *C07C 4/04* | (2006.01) | |
| *B01J 19/24* | (2006.01) | |
| *C07C 5/327* | (2006.01) | |
| *B01J 8/04* | (2006.01) | |
| *C07C 11/04* | (2006.01) | |
| *C10G 9/26* | (2006.01) | |
| *C07C 5/32* | (2006.01) | |

(52) U.S. Cl.
CPC ........... *B01J 19/24* (2013.01); *B01J 19/2415* (2013.01); *B01J 19/2485* (2013.01); *C07C 5/32* (2013.01); *C07C 5/327* (2013.01); *C07C 11/04* (2013.01); *C10G 9/26* (2013.01); *B01J 2208/00513* (2013.01); *B01J 2208/00548* (2013.01); *B01J 2219/00076* (2013.01); *B01J 2219/00087* (2013.01); *B01J 2219/00164* (2013.01); *B01J 2219/24* (2013.01)

(58) Field of Classification Search
CPC .... B01J 2219/00087; B01J 2219/00164; B01J 2219/24; B01J 2208/00513; C07C 4/04; C07C 5/327; C07C 11/04; C10G 9/26
USPC .................................. 585/501, 650; 422/116
See application file for complete search history.

(56) References Cited

U.S. PATENT DOCUMENTS

| | | |
|---|---|---|
| 2,678,339 A | 5/1954 | Harris |
| 2,692,818 A | 10/1954 | Bewick |
| 2,692,819 A | 10/1954 | Hasche et al. |
| 2,956,864 A | 10/1960 | Coberly |
| 2,967,205 A | 1/1961 | Coberly |
| 3,024,094 A | 3/1962 | Coberly |
| 3,093,697 A | 6/1963 | Kasbohm et al. |
| 3,258,455 A | 6/1966 | Natta et al. |
| 3,305,538 A | 2/1967 | Natta et al. |
| 3,364,190 A | 1/1968 | Emrick |
| 3,645,992 A | 2/1972 | Elston |
| 4,076,698 A | 2/1978 | Anderson et al. |
| 4,243,691 A | 1/1981 | Mohlenkamp, Jr. et al. |
| 4,302,565 A | 11/1981 | Goeke et al. |
| 4,659,685 A | 4/1987 | Coleman, III et al. |
| 5,019,143 A | 5/1991 | Mehrta |
| 5,082,481 A | 1/1992 | Barchas et al. |
| 5,452,581 A | 9/1995 | Dinh et al. |
| 5,672,197 A | 9/1997 | Rothchild |
| 5,892,079 A | 4/1999 | Wilson, Jr. |
| 5,904,880 A | 5/1999 | Sun |
| 5,927,063 A | 7/1999 | Janda et al. |
| 5,960,643 A | 10/1999 | Kuechler et al. |
| 6,069,288 A | 5/2000 | Ou et al. |
| 6,121,503 A | 9/2000 | Janssen et al. |
| 6,271,428 B1 | 8/2001 | Cottrell |
| 6,293,999 B1 | 9/2001 | Cheng et al. |
| 6,593,506 B1 | 7/2003 | Searle |
| 7,491,250 B2 | 2/2009 | Hershkkowitz et al. |
| 7,846,401 B2 | 12/2010 | Hershkkowitz et al. |
| 8,524,159 B2 | 9/2013 | Herskkowitz et al. |
| 2007/0144940 A1 | 6/2007 | Hershkowitz et al. |
| 2007/0191664 A1 | 8/2007 | Hershkowitz et al. |
| 2008/0142409 A1 | 6/2008 | Sankaranarayanan et al. |
| 2009/0008292 A1 | 1/2009 | Keusenkothen et al. |
| 2011/0291051 A1 | 12/2011 | Hershkowitz et al. |
| 2013/0211169 A1 | 8/2013 | Hershkowitz |

\* cited by examiner

HYDROCARBON CONVERSION TO ETHYLENE

CROSS REFERENCE TO RELATED APPLICATIONS

This application is a Divisional Application of U.S. patent application Ser. No. 14/942,287, filed Nov. 16, 2015, now U.S. Pat. No. 9,499,457, which claims the benefit of U.S. Patent Application Ser. No. 62/093,003, filed Dec. 17, 2014, and European Patent Application No. 15153727.1, filed Feb. 4, 2015, the disclosures of which are incorporated by reference in their entireties.

FIELD OF THE INVENTION

This invention is directed to hydrocarbon conversion processes and reactors for producing ethylene. In particular, this invention is directed to low temperature, high hydrocarbon partial pressure pyrolysis for producing ethylene.

BACKGROUND OF THE INVENTION

Olefins, or alkenes, are a homologous series of hydrocarbon compounds characterized by having a double bond of four shared electrons between two carbon atoms. Because of their availability, reactivity and versatility, olefins, especially the light olefins like ethylene, propylene, butenes and butadiene, continue to experience tremendous growth in demand. Ethylene, the simplest olefin member, continues to be the largest volume olefin produced.

Commercial production of ethylene is almost exclusively accomplished by pyrolysis of hydrocarbons (e.g., thermochemical decomposition of hydrocarbon feed at elevated temperatures in the absence of oxygen) in tubular reactor coils installed in externally fired heaters. Pyrolysis feedstocks include hydrocarbons such as ethane, propane or hydrocarbon liquids ranging in boiling point from that of light straight-run gasoline through gas oil through heavy oils.

The pyrolysis or thermal cracking process to produce ethylene is generally an endothermic equilibrium reaction. As an example, thermally cracking ethane to produce ethylene involves the endothermic equilibrium reaction:

$$C_2H_6(g) \leftrightarrows C_2H_4(g) + H_2(g) \ \Delta H = +138 \text{ kJ mol}^{-1}$$

Since the pyrolysis process involves endothermic equilibrium reactions, Le Chatelier's Principle suggests that high equilibrium yields of olefin products will be favored by carrying out the process at higher temperatures and lower pressures.

Because of the very high temperatures employed in carrying out pyrolysis reactions, commercial ethylene production processes invariably produce significant amounts of by-products such as acetylene, butadiene and benzene. Typically these are removed from the ethylene, e.g., so that the ethylene can be used in other conversion processes. By-product production is also problematic because they can produce high amounts of coke at pyrolysis temperatures. Coke formation is undesirable, because it can cause increased reactor pressure drop and substantial loss in heat transfer.

Steam is typically added to the pyrolysis feedstock in order to simultaneously increase ethylene yield and reduce coke accumulation. The addition of steam reduces the partial pressure of the hydrocarbon portion of the feedstock, thereby lowering reactant feed pressure to increase selectivity to ethylene. The steam also lessens coke accumulation. The amount of steam used per pound of feed in the thermal cracking process depends to some extent on the hydrocarbon feed used. Typically, steam pressures are in the range of about 30 lbs. per sq. in. (psig, 207 kPag) to about 80 psig (552 kPag). The amount of steam added is typically in the range of about 0.2 lbs of steam per pound of total hydrocarbon feed (0.09 kg/kg) to 0.7 lbs. of steam per pound of total hydrocarbon feed (0.32 kg/kg).

In a steam cracking furnace, a mixture of hydrocarbon and steam is typically subjected to temperatures of about 750° C. to 900° C., with the hydrocarbon being converted by a pyrolysis reaction to produce an effluent gas mixture typically comprising ethylene, methane, hydrogen and unconverted feed, as well as some hydrocarbons heavier than the feed. The effluent gas is cooled, e.g., by indirect contact with cooling water and/or by direct contact with circulated cooled quench oil and/or circulated cooled water. These cooling steps typically condense and at least partially remove relatively heavy hydrocarbons in the effluent stream, typically in the naphtha range and heavier.

The uncondensed cooled gas portion of the effluent stream contains ethylene and other gases having relatively close boiling points to ethylene. The effluent gas stream is typically compressed in one or more compressor stages (typically 3-5 stages) to an elevated pressure. The effluent from each stage is typically cooled against an ambient temperature medium and any condensed liquids removed before entering the subsequent compression stage. Acid gases such as $H_2S$ and $CO_2$ are generally removed after at least one of these stages of compression, for example through the use of a caustic contacting tower or an amine scrubbing system. Once compressed, scrubbed and dried, the furnace effluent gas enters the separation section for recovering ethylene.

The separation section typically employs a number of distillation towers for the purpose of recovering ethylene from the various other compounds in the effluent gas and purifying the ethylene sufficiently for use in downstream processes, such as the manufacture of polyethylene. A number of alternatives exist for the design of the ethylene separation section. Typically, ethylene separation designs will employ at least a deethanizer tower which has the purpose of separating $C_2$ and $C_3$ components (that is, ethylene and ethane from propylene and propane, respectively), a demethanizer tower for separating $C_2$ components from any components lighter than the $C_2$ components, and a $C_2$ splitter for the final separation of ethylene from ethane. For example, ethane-ethylene separation can be carried out at the $C_2$ splitter at a temperature of about −30° C. to −20° C. and a pressure of about 300 psig (2068 kPag) to 350 psig (2413 kPag).

Methods of increasing the overall equilibrium production of ethylene from pyrolysis reactions are desired. In particular, ethylene pyrolysis production processes are desired, which reduce overall energy consumption. More particularly, ethylene pyrolysis production processes are desired, which reduce the compression energy needed in downstream processing to more effectively separate ethylene from various similar boiling point by-products such as ethane, acetylene and propylene.

SUMMARY OF THE INVENTION

Certain aspects of the invention relate to hydrocarbon pyrolysis processes and reactors, which increases the overall equilibrium production of ethylene from typical pyrolysis. The ethylene production pyrolysis processes can be carried out at reduced overall energy consumption compared to current processes. In particular, the pyrolysis processes can be carried out at relatively higher hydrocarbon partial pressures for a relatively short period of time to produce relatively high quantities of ethylene compared to current processes for producing ethylene. Configuring the pyrolysis reactor for carrying out the pyrolysis reaction at relatively higher hydrocarbon partial pressures can reduce the compression energy needed downstream of a typical conversion process, which can result in more effective and efficient separations of ethylene from various similar boiling point by-products such as ethane, acetylene and propylene.

According to one aspect of the invention, there is provided a hydrocarbon conversion process. The process comprises providing a pyrolysis feed comprising hydrocarbon, wherein the hydrocarbon comprises ethane and/or $C_{3+}$ hydrocarbon. Also provided is a reactor including (i) at least one thermal mass and (ii) having a first zone, a second zone, and a reaction zone intermediate to the first and second zones.

The pyrolysis feed can be passed from the first zone to the second zone of the reactor, with heat being transferred from thermal mass located proximate to the first zone to the pyrolysis feed as the pyrolysis feed is passed through the reactor. The pyrolysis feed can be passed proximate to the thermal mass at a peak pyrolysis temperature in the reaction zone in the range of from 850° C. to 1200° C., at a hydrocarbon partial pressure ≥7 psia, to convert ≥10.0 wt. % of the hydrocarbon in the pyrolysis feed into a pyrolysis product. The pyrolysis product can comprise $C_2$ unsaturates having an ethylene:acetylene molar ratio ≥1:1. The process can be quenched by transferring heat from the pyrolysis product to thermal mass located proximate to the second zone to cool the pyrolysis product to a temperature below the peak pyrolysis temperature. The thermal mass proximate to the first zone and the thermal mass proximate to the second zone can be regions of the same thermal mass or, alternatively, they can be separate thermal masses.

According to another aspect of the invention, the reactor can be a reverse-flow reactor, with the pyrolysis feed being passed to the reverse-flow reactor during a first time interval to produce the pyrolysis product. During a second time interval, a provided combustion feed comprising hydrocarbon fuel and oxidant can be passed to the reverse-flow reactor. Heat can be transferred from the second zone to the combustion feed, and the heated combustion feed can be exothermally reacted, typically proximate to the reaction zone, to produce combustion products and heat. Heat can be transferred from the combustion reaction to the first zone to cool the combustion products. Thermal mass located in the zones receives, stores, and releases the transferred heat.

In certain aspects, the pyrolysis feed is passed through the thermal mass at a total gas residence time in the thermal mass of ≤1.0 second. Alternatively or in addition, the pyrolysis feed can be passed through the thermal mass at a total gas residence time above 800° C. in the reaction zone of thermal mass of ≤0.100 second.

In other aspects, the hydrocarbon of the pyrolysis feed can comprise ≥50 wt. % ethane, based on total weight of the hydrocarbon in the pyrolysis feed. The pyrolysis product can include unreacted hydrocarbon from the pyrolysis feed. The pyrolysis feed can also comprise diluent, and the pyrolysis product can comprise unreacted diluent.

More particularly, the hydrocarbon of the pyrolysis feed can comprise ≥90.0 wt. % ethane. The pyrolysis feed can also include diluent comprising ≥90.0 wt. % methane, and the reaction zone can be at a total pressure ≥120 psig (18.2 bar gauge, "barg"). Alternatively, the diluent of the pyrolysis feed can comprise ≥90.0 wt. % water, and the reaction zone can be at a total pressure ≥40 psig (2.7 barg).

The hydrocarbon conversion process can further include a step of separating $C_2$ unsaturates from the pyrolysis product. The separating can be carried out (i) without increasing total pressure of the pyrolysis product or (ii) increasing total pressure of the pyrolysis product by a factor of ≤2.0 or ≤5.0.

In other aspects, pyrolysis feed can be passed through the thermal mass at a peak pyrolysis temperature in the range of from 900° C. to 1100° C. and a hydrocarbon partial pressure ≥20 psia. In these or in alternative aspects, the pyrolysis feed can be passed through the thermal mass at a total gas residence time in the thermal mass of ≤0.75 seconds to convert ≥50.0 wt. % of the pyrolysis feed's hydrocarbon to $C_2$ unsaturates.

Although the invention can be described in terms of hydrocarbon conversion processes, particularly pyrolysis reaction processes, for producing olefins such as ethylene, the invention is not limited thereto. In other words, to the extent that the following detailed description is specific to a particular embodiment or a particular use, this is intended to be illustrative only, and is not to be construed as limiting the scope of the invention. On the contrary, it is intended to cover all alternatives, modifications and equivalents that may be included within the spirit and scope of the invention, as defined by the appended claims.

DETAILED DESCRIPTION OF THE INVENTION

I. Pyrolysis Reaction

Certain aspects of the invention relate to hydrocarbon conversion processes, as well as to reactors configured to carry out such hydrocarbon conversion processes. In particular, the hydrocarbon conversion process can include a pyrolysis process, which is an endothermic reaction for thermally breaking (i.e., cracking) C—C and/or C—H bonds.

The pyrolysis process of this invention typically increases the overall equilibrium production of ethylene compared to typical pyrolysis reactions. The pyrolysis process of this invention can be carried out at low or non-severe temperature profiles, meaning that the conversion process can be effectively carried out at temperatures of less than 1200° C. for relatively short periods of time. Thus, special materials for very high or severe temperature processes are not required.

Since the pyrolysis of the invention can be carried out at higher hydrocarbon partial pressures than conventional pyrolysis, the downstream separation of ethylene from various similar boiling point by-products such as ethane, acetylene and propylene can be effectively carried out using lower duty compressors. Thus, energy consumption can be substantially reduced.

Although the type of reactor is not critical, the process is particularly suited to pyrolysis reactors such as regenerative reactors that include thermal masses, particularly regenerative, reverse-flow reactors. For instance, the regenerative, reverse-flow reactor may have a single thermal mass or at least two thermal masses in fluid communication with each other and in series, one with the other. The invention may be particularly beneficial for pyrolysis processes that utilize a cyclical process that involves repeating a heating step, pyrolysis step and any other steps, if any, in each cycle.

Although regenerative or regenerative reverse-flow reactors have been used in pyrolysis reactions, the reactions are typically carried out at conditions favorable for producing acetylene. For example, the "Wulff" reactor, as described in the IHS, SRI Consulting's Process Economics Program "Acetylene" Report Number 16 (1966) and 16A (1982), and the reactors described in U.S. Pat. Nos. 2,319,679; 2,678,339; 2,692,819; 2,956,864; 2,967,205; 3,024,094; 3,093,697; and GB 830,574, are typical reverse-flow pyrolysis reactors. These reactors are configured to operate at temperatures of greater than 1200° C. and hydrocarbon partial pressures of not greater than 7 psi to produce alkynes, such as acetylene.

Configuring a reactor such as a regenerative or regenerative reverse-flow reactor to carry out pyrolysis reactions at lower temperatures and higher hydrocarbon partial pressures has the unforeseen effect of substantially shifting the equilibrium yield of the pyrolysis reaction to favor ethylene production over acetylene production. Thus, this invention involves configuring a reactor to carry out a reaction process that runs counter to the well-established Le Chatelier's Principle, which suggests that high equilibrium yields of olefin products will be favored by carrying out the process at higher temperatures and lower hydrocarbon partial pressures. Running the pyrolysis reactor at higher hydrocarbon partial pressure provides a further benefit by enabling the reduction of the compression energy needed downstream of the conversion process in order to more effectively and efficiently separate ethylene from various similar boiling point by-products such as ethane, acetylene and propylene.

II. Pyrolysis Reactor

The pyrolysis reaction of this invention is carried out in a reactor capable of temperature, pressure and contact time constraints for producing commercial quantities of ethylene from a pyrolysis reaction. A reactor refers to equipment used for chemical conversion. As such, several items identified as reactors may be combined to become a single entity that is also identified as a reactor, in that individual and combined entities may be characterized as equipment used for chemical conversion.

A pyrolysis reactor refers to equipment for converting hydrocarbons by pyrolysis chemistry. Pyrolysis or pyrolysis chemistry involves the conversion of hydrocarbons to unsaturates, particularly $C_2$ unsaturates such as ethylene and acetylene, which is an endothermic reaction requiring addition of heat.

The pyrolysis reactor may include one or more reactors and/or associated equipment and lines. That is, in certain aspects, the pyrolysis reactor includes one or more thermal mass (e.g., one thermal mass or at least two thermal masses in fluid communication with each other and in series, one with the other or may include two thermal masses in series within a single reactor). Examples of such reactors include, but are not limited to, reverse-flow regenerative reactors as those described in U.S. Patent App. Pub. No. 2007/0191664; and pyrolysis reactors as described in U.S. Pat. No. 7,491,250 and U.S. Patent App. Pub. Nos. 2007/0144940 and 2008/0142409.

The terms "crack" and "cracking" may be used interchangeably with the terms pyrolyze and pyrolysis. In a thermal pyrolysis reaction, 50%, 80%, or 90%, of this heat is provided by heat transfer from the reactor, e.g., from solid surfaces, such as tubulars or bed materials. Any combustion chemistry that occurs within the pyrolysis stream of a pyrolysis reactor provides a minority of the endothermic heat of pyrolysis, such as <50%, <20%, or <10% of the endothermic heat of pyrolysis.

A zone, as used herein, refers to a location within the pyrolysis reactor, which may include one or more reactor components and/or associated equipment and lines. The zone may include a specific volume within a reactor, a specific volume between two reactors and/or the combination of different disjointed volumes in one or more reactors. Although the thermal pyrolysis reverse-flow regenerative reactors described herein may comprise a single thermal mass, reactors which include two or more thermal masses or other suitable configurations are within the scope of the invention.

A reaction zone, alternatively referred to as pyrolysis zone, is a location in the thermal pyrolysis system where >50%, >75% and/or >90% of the conversion of hydrocarbons into $C_2$ unsaturates in the pyrolysis system is performed. That is, while some thermal cracking may occur upstream of reaction zone, the reaction zone is the location or volume within the reactor where a substantial amount of the smaller molecules are produced from the initial hydrocarbons provided to the reactor. For example, the reaction zone for a steam cracking system is in the radiant tubes of the steam cracking furnace, while the reaction zone is generally a central location of a reverse-flow regenerative reactor. Thermal mass can be located proximate to the central location. Thermal mass can also be located proximate to any mixing components disposed between one or more zones.

In certain pyrolysis reactors (e.g., steam cracking furnace configuration), the heating and the pyrolysis process occur simultaneously, for example with a combusting stream on one side of partition (typically a wall or tubular) and the pyrolysis stream on the other side. Such reactors operate at or near steady state. The partition between the combustion feed (e.g., reactants used during a heating step) and the pyrolysis feed have real physical dimensions, and the temperature is not equal at every location. For example, on the combustion side, temperatures may be hottest near a flame region (e.g., burner), and on the pyrolysis side temperatures increase with heat addition until some maximum temperature is reached. Steady state in these systems means that, at any given location relative to the fixed partition, temperatures remain relatively steady. However, the gases that travel through the reactor are heated and cooled by the reactions and heat transfer that takes place in the reactor.

The term "peak pyrolysis temperature" means the maximum temperature achieved by the pyrolysis stream gases (e.g., total gas stream comprising feed and product components) as the gases travel through the pyrolysis reactor (e.g., proximate to one or more thermal mass in the reactor).

The "pyrolysis temperature" can be considered the temperature of the gases in the reaction zone of the pyrolysis reactor, which can be measured by a device (such as a thermocouple) that is not in contact with the thermal mass material. For example, for pyrolysis feed being passed to and traveling through tubulars or through channels in a thermal mass of a pyrolysis reactor, the pyrolysis gas temperature may be taken as the average temperature at a tubular or channel cross-section over which total gas (e.g., feed and converted product gases) passes. The peak pyrolysis gas temperature can be considered the highest cross-sectional-average temperature in the tubular or channel cross-section.

Reverse-flow regenerative reactors may involve multiple steps repeated in sequence to form a cycle for the process. The process may include a heating step to heat the thermal mass of the reverse-flow reactor and a pyrolysis step that converts the hydrocarbons into the reaction product. The steps may involve passing the respective streams over a solid material in fixed orientation (e.g., one or more thermal masses), which utilizes valves to alternate introduction of hydrocarbon in the pyrolysis stream and/or combustion streams into the internal portion of the reactor.

In certain aspects, the processes are carried out cyclically, e.g., by repeating a heating step, pyrolysis step and any other steps, if any, in each cycle, as part of the hydrocarbon processing mode. The process may include various steps during a hydrocarbon processing mode and a non-operational mode. The hydrocarbon processing mode may refer to the steps utilized by the reactor system to convert hydrocarbons in the feed into useful products, such as $C_2$ unsaturates. For instance, as noted above, the steps in a cyclical process of the hydrocarbon processing mode may involve repeating a heating step, a pyrolysis step and any other steps, if any, in each cycle. These steps may include a flushing step and/or heating step that removes at least a portion of non-volatiles from the reactor as part of the cycle. Alternatively, a non-operation mode may be utilized for reactor cleaning operations. The non-operational mode typically involves interrupting the flow of hydrocarbons to decoke the furnace, or reactor, where decoking refers to removal of at least a portion of coke deposited on various surfaces of the reactor system.

The cycle may be performed continuously, semi-continuously, or even as a batch operation. Accordingly, a cycle includes the time spent in heating step plus time spent in pyrolysis step plus any time needed to switch between steps or for additional steps before the repeat of the sequence. Typical cycle times may be in the range of 1 to 60 seconds, or in the range of 1 to 30 seconds. The heating and pyrolysis steps may have equal durations or may be adjusted to have different durations. Shorter cycle times may be beneficial in certain cases in order to avoid a significant buildup of non-volatile compounds in the pyrolysis step. These non-volatile compounds can be subsequently swept away in the transitional step or combusted though change of operating conditions.

The thermal mass typically comprises one or more materials which facilitate the process of heat addition and removal. Such materials can be in the form of a network of passages that are used by the gases in each step to transit the region containing solid material. The heat addition step leaves a profile of temperatures in the solid material, that is, a temperature that varies along the path by which the gases transit the solid material. The shape of that profile depends on many factors, including if and where a heat release (combustion) reaction occurs, the initial temperature distribution, the duration of the heating step, the flow rate and inlet temperature of the gas stream, and the heat capacity and transfer properties of the gas and solid material. On average, the solid material is hottest at the end of the heating step. The pyrolysis step consumes heat and reduces the solid material's average temperature. The pyrolysis step changes the profile of temperatures in the solid material, in a way that depends on many factors, including where the heat consumption (pyrolysis) reaction occurs, the initial temperature distribution, the duration of the pyrolysis step, the flow rate and inlet temperature of the gas stream, and the heat capacity and transfer properties of the gas and solid. Fixed-solid regenerative pyrolysis reactors do not operate in the steady state. That is, at any given location, the temperature changes. However, these reactors may be in a periodic steady state, meaning that the same cycling of temperatures occurs over and over as the reactor sequentially repeats the heating and pyrolysis steps.

A regenerative, reverse-flow reactor can be considered (i) "reverse flow" in the sense that an upstream region of the reactor with respect to the average flow of a first feed mixture corresponds to the downstream region with respect to the average flow of a second feed mixture and (ii) "regenerative" in the sense that at least a portion of any heat removed from the reactor's thermal mass by transfer to endothermic reactions during a first interval is restored to the thermal mass by heat released in a second interval (and vice versa). For example, during at least one time interval, the reverse-flow reactor exothermically reacts a combustion feed mixture, and stores at least a portion of the heat of combustion in an internal volume of the reactor, e.g., in thermal mass. In other words, the internal volume typically includes at least one thermal mass comprising heat transfer material for transferring heat to and from combustion feed, combustion products, pyrolysis feed, and pyrolysis products flowing through the reactor.

A variety of regenerative reverse-flow reactors can be utilized. For example, a reverse-flow reactor may include a housing, a plurality of flow-controls (e.g., conduits and valves), one or more insulation components (e.g., insulation bricks) and one or more process flow components (e.g., thermal mass, mixing components, etc.). The housing can be utilized to enclose an interior region and have one or more insulation components disposed adjacent to the housing. The plurality of flow-controls may include one or more conduits, one or more apertures, and one or more valves that are configured to manage the flow of one or more streams into and out of the interior region from a location external to the interior region or housing. Process flow components can be configured and/or arranged to manage the flow of fluids through the interior region. For example, certain process flow components may include a thermal mass having a plurality of portions (e.g., a plurality of segments) with each having different flow passages and a wetted area. One or more mixer or mixer-distributors can be used for mixing feed components.

Regenerative, reverse-flow reactors may involve multiple steps repeated in sequence to form a cycle for the process. That is, steps that execute hydrocarbon conversion chemistry in forward-flow may be alternated with regeneration steps in reverse-flow to preheat, heat, or reheat the thermal mass. The steps may involve passing mixtures over a solid material in fixed orientation (e.g., one or more thermal masses or portions thereof). As part of these steps, valves can be utilized to alternate introduction of a first feed mixture and/or a second feed mixture into the interior region of the reactor to contact the thermal mass.

As an example, a reverse-flow regeneration step can be used between successive forward-flow hydrocarbon conversion steps. During the regeneration step, a combustion feed comprising a fuel and oxidant can be delivered to a location along the flow path within the reactor (e.g., a mixing zone). The delivered fuel and oxidants in the combustion feed then exothermically react (combust) and heat at least a portion of the thermal mass. According to one aspect of this invention, the combustion reaction can be carried out to heat the thermal mass or masses of the reactor before, or after one or more intervals of the hydrocarbon conversion (pyrolysis) reaction. For example, a combustion reaction can be carried out to initially heat (e.g., preheat) at least one thermal mass of the reverse-flow reactor. Combustion products can then be exhausted, e.g., by flushing them from the reactor with a flushing fluid such as an inert gas.

Following reactor regeneration, a first feed mixture (a pyrolysis feed) can be introduced into the reactor and exposed to a heated thermal mass located proximate to the first zone to heat the hydrocarbon in the first feed mixture. As the heated first feed mixture flows downstream toward a second zone, hydrocarbon conversion (pyrolysis) is carried out in a reaction (pyrolysis) zone of the reactor. The pyrolysis zone is typically located intermediate to (e.g., entirely between) the first and second zones. Reaction products and/or unreacted hydrocarbon in the feed mixture can then be quenched in the second zone as they flow through the reactor to halt the pyrolysis reactions to produce reaction or pyrolysis products. The quenching can be accomplished, e.g., by transferring heat to a cooler region of the reactor's thermal mass or to a second thermal mass located downstream (with respect to forward-flow) of the first thermal mass (e.g., a quenching zone), obviating the need for an external quench as in a conventional steam cracker. For example, the reverse-flow reactor can contain a second thermal mass (located e.g., proximate to the quenching zone) that is cooler than the thermal mass located proximate to pyrolysis zone—where the pyrolysis is carried out at approximately the peak pyrolysis gas temperature. The flow of the feed/conversion streams is configured so that the cooler thermal mass zone is located in a downstream flow direction (during forward-flow) relative to the location of the reaction zone of thermal mass in which the peak pyrolysis gas temperature is reached (e.g., pyrolysis zone). In operation, the cooler thermal mass zone absorbs heat from the pyrolysis product mixture during a first time interval, sufficient to (i) cool or quench the product mixture from pyrolysis of hydrocarbon in a first feed stream and (ii) impart heat to a fuel and oxidant streams of the re-heating step, when the flow is reversed during a second time interval (reverse-flow).

The reverse-flow reactor can include reactor components, such as process flow components (e.g., reactor components used to manage the flow of mixtures through the reactor, one or more thermal masses for absorbing, storing and releasing heat and mixing components) and insulation components (e.g., reactor components used to manage the heat transfer from the process flow within the reactor to the external surface of the reactor, such as insulation bricks, tiles or packing). The reactor components can be formed from different materials, such as refractory support materials.

The heat generated during the combustion step may preferably be stored in the thermal mass material for use in a subsequent pyrolysis step. The thermal mass material can be, e.g., designed or adapted to facilitate storage and utilization of heat.

In certain aspects, the thermal mass is a material (e.g., a solid) that can transfer (e.g., absorb, store, and release) thermal energy over a temperature range for carrying out the reverse flow cycle, which includes the pyrolysis reaction and any optional combustion reaction. For example, the thermal mass can be a solid material that can absorb, release, and store heat to and/or from reactants and products over a temperature range in which pyrolysis can be carried out, including those that do so without any significant phase change. Examples of temperature ranges at which the thermal mass absorbs, stores and releases thermal energy include a range of from 50° C. to 1500° C., alternatively from 100° C. to 1500° C. or from 200° C. to 1500° C., or 250° C. to 1200° C., or 300° C. to 1100° C.

The thermal mass can be characterized by one or more properties. Examples of such properties include, but are not limited to, melting temperature, porosity, bulk density, thermal conductivity, thermal expansion and thermal capacity.

Melting temperatures (melting points) are reflective of the ability of the thermal mass to withstand combustion and pyrolysis temperatures without chemical change and/or physical destruction. Thermal masses having higher melting points are preferred according to this invention. For example, the melting point of the thermal mass of this invention is preferably at least 1200° C., or at least 1500° C.

Geometric void denotes the void volume in major passages of the thermal mass that gases use to transit the reactor, and exclude volumes than may be present in small pores within the walls of the reactor contents. For example, for honeycomb monoliths, geometric void volume includes the volume in the channels, but excludes any pore volume that may exist in the channel walls. For honeycomb monoliths, the term 'open frontal area' is also used in the art to reflect the geometric void. Geometric void is most frequently expressed as a percent of total (solid and void) volume of the object being described. Geometric solid can be considered the filled volume that is not used by gases to transit the reactor. For example, in honeycomb monoliths, the channel walls are considered the geometric solid. For packed beds, the bed packing particles such as spheres, pellets or extrudates (cylinders) are considered the geometric solid, and the gas space between the particles are considered the geometric void.

As an example, the thermal masses utilized in certain embodiments of this invention can have a geometric void between about 10% and 70%, such as between 20% and 60%. Pore volume or porosity within the geometric solid, such as within channel walls of the thermal masses, is preferably minimized to improve thermal properties as discussed below. As an example, the thermal masses utilized in certain embodiments of this invention can have a pore volume within the geometric solid of not greater than 20%, or not greater than 10%, or not greater than 5%.

Bulk density is a measure of the weight of a given volume of the thermal mass. Higher bulk densities, with lower geometric void fraction, can be particularly effective. As an example, the thermal mass utilized in certain embodiments of this invention can have a bulk density of at least 0.5 g/cm$^3$. For example, the bulk density can be from 0.5 g/cm$^3$ to 5 g/cm$^3$ or from 1 g/cm$^3$ to 3 g/cm$^3$.

Thermal conductivity is defined as the quantity of heat that will flow through a unit area in direction normal to the surface area in a defined time with a known temperature gradient under steady state conditions. Thermal conductivity represents a general heat flow characteristic of the geometric solid of the thermal mass. Higher thermal conductivity thermal masses are preferred. For example, the geometric solid of the thermal mass can have a thermal conductivity of from 0.1 W/mK to 50 W/mK or from 0.5 W/mK to 30 W/mK.

Thermal expansion of the thermal mass should not be so great such that cracking of the material occurs during operation of the reaction system. In one aspect, the thermal mass can be characterized by a thermal expansion coefficient. For example, the thermal mass can have a thermal expansion coefficient of from $0.1 \times 10^{-6}$/K to $20 \times 10^{-6}$/K or from $0.2 \times 10^{-6}$/K to $15 \times 10^{-6}$/K. In this example, the thermal expansion coefficient is given as a value in a temperature range of from 25° C. to 800° C.

Thermal capacity is the ability of a material to hold heat. The thermal masses utilized in certain embodiments of this invention preferably has a higher thermal capacity, but not so high as to increase the probability of cracking at higher temperatures. For example, the thermal masses utilized in certain embodiments of this invention can have a thermal capacity of from 250 $J/dm^3K$ to 4500 $J/dm^3K$ or from 500 $J/dm^3K$ to 3000 $J/dm^3K$.

Checker bricks, tiles, and monoliths can be used as to form the reactor's thermal mass, or portions, regions, and segments thereof. Such materials can be in the form of or can be arranged to form a network of passages that are used by the gases in each step to transit one or more regions of the reactor. The thermal mass can be a ceramic, which may include yttria, zirconia, alumina, and/or other refractory material capable of adsorbing, storing and transferring heat, and that are effective in withstanding temperatures within the pyrolysis reactor.

Wetted area is the surface over which heat is transferred from geometric solid to the gas in the geometric void, and has units of geometric surface area per bulk volume of thermal mass (pore volume within the geometric solid is excluded). Typically, thermal mass having a high surface area per unit volume is used to aid achieving a relatively quick change in the temperature through the reactor. The thermal mass can provide an average wetted surface area per unit volume that ranges from about 1 $cm^{-1}$ to about 100 $cm^{-1}$, e.g., from about 3 $cm^{-1}$ to 80 $cm^{-1}$, and such as from about 5 $cm^{-1}$ to 50 $cm^{-1}$.

The thermal mass can include separate passages to manage the flow of hydrocarbon components and or oxidant through the reactor and reactor components, regions, and zones. Multiple thermal masses can be arranged to accommodate heat flow to heat the feed mixture and quench the reaction products. Typically, each thermal mass includes separate passages. The separate flow passages in the thermal mass can further comprise flow barriers that effectively function as walls to lessen or prevent cross flow or mixing of fluids (e.g., reactants, oxidants, and/or products) between passages, except in the desired regions of the reactor. Each thermal mass preferably includes multiple passages, which may preferably be in parallel flow arrangement. The channeled thermal mass may preferably be comprised of one or more honeycomb monoliths. Preferred honeycomb monoliths are structures that comprise many (e.g., a plurality, meaning more than one) gas flow passages, arranged in parallel fashion with walls serving to separate each passage. Such reactor can include a single monolith or a plurality of monoliths. Each monolith can be formed by extruding or die pressing monolith blocks with shaped (e.g., square or hexagonal) cross-section and two- or three-dimensionally stacking, such blocks above, behind, and beside each other. Monoliths are particularly effective as thermal mass because they provide high heat transfer capacity with lessened pressure drop.

III. Heating Step of a Reverse Flow Reactor

In certain aspects, the pyrolysis is carried out in a reverse-flow pyrolysis reactor. The process can include a heating step to heat the thermal mass and a pyrolysis step that converts the hydrocarbons in the reaction zone into the reaction product using heat stored in thermal mass during the heating step.

In the heating step, combustion feeds can be supplied to or injected into a reactor end zone (e.g., at or adjacent to a first end of the first and/or second zone of the reactor). The combustion feed streams (e.g., fuel and oxidant) may flow through separate conduits through a combustion preheat zone (e.g., through a portion of the thermal mass) to the reaction zone, where the combustion feed streams combine and exothermically react to heat the reaction zone. In other aspects, one combustion feed stream may flow through the reactor and another may be supplied directly to the reaction zone. Typically, the combustion feed streams include a hydrocarbon fuel stream and an oxidant stream, which are maintained substantially separate until passing to the reaction zone, and which are capable of reacting together and combusting to supply or generate heat and produce combustion products.

The combustion feed streams may include two or more individual feeds that are to be combined to form a mixed combustion feed of the two or more feed streams, such as a hydrocarbon fuel that does not contain oxidant (e.g., $O_2$) or non-combustible non-volatiles and a combustion oxidant that may include an oxygen or oxygen containing fluid. The hydrocarbon fuel may be a hydrogen-containing composition of hydrogen, hydrocarbon or a mixture thereof. The hydrocarbon can be the same or different from the hydrocarbon used in the pyrolysis feed. Additional or further specific examples of hydrocarbon fuel compositions that can be used as a combustion feed component include, but are not limited to, hydrogen, methane, ethane, ethylene, propane, propylene, butane, butylene, hexane, heptane, methanol, ethanol, propanol, butanol, dimethyl ether, diethyl ether, liquid natural gas (LNG), liquid petroleum gas (LPG), naphtha, gasoline, kerosene, light gas oil, heavy-oil decomposition components having a final ASTM D 86 boiling point of not greater than 565° C., natural gas, coal bed methane, landfill gas, blast furnace gas, coke oven gas, converter gas, by-product gas derived from a chemical plant, gas obtained by gasification of coal or heavy oil, coal carbonization gas, water gas from the gasification of coal, coal partial-combustion gas, light oil or gas obtained by thermal separation of heavy oil, heavy-oil thermal decomposition light-oil or gas, heavy-oil oxidation decomposition light-oil or gas, super-heavy oil thermal decomposition light-oil or gas, super-heavy oil oxidation decomposition light-oil or gas, fermentation gas, including mixtures of one or more of these substances.

The oxidant may comprise an oxygen composition that has sufficient oxygen content to enable the hydrocarbon fuel to combust. Oxidant can be supplied in any form suitable for combustion, such as pure oxygen or in the form of air. The oxidant may include, but not limited to, air, oxygen or mixtures thereof. The oxidant can be oxygen in air, for example.

The combustion feed may additionally include non-combustible but volatile diluents such as $N_2$, $CO_2$, $H_2O$, and/or other inert gases.

The combustion feed typically comprises oxygen in an amount of at least 80% of stoichiometric for complete combustion of hydrocarbon fuel composition. For example, the combustion feed can comprise oxygen in a stoichiometric amount for complete combustion of the hydrocarbon fuel composition in the combustion feed, or preferably in an amount in excess of stoichiometric for complete combustion of the hydrocarbon fuel composition in the combustion feed.

The hydrocarbon fuel component of the combustion feed stream and the oxidant component of the combustion feed stream can be mixed at or prior to entering the reaction zone. That is, the combustion feed stream components can be initially flowed to the reaction zone through a combustion preheat zone in separate channels of a thermal mass (located, e.g., a portion of the first and/or second zone of the reactor). For example, the hydrocarbon fuel stream and oxidant stream can be separately introduced into the reactor and separately flowed through separate channels of a honeycomb channel arrangement in portions of the thermal mass that are located upstream of the reaction zone. The hydrocarbon fuel stream and oxidant stream are typically heated as they flow through the channels, e.g., by heat transferred to these portions during quenching of pyrolysis products during a preceding pyrolysis step. Following heating, the hydrocarbon fuel stream and the oxidant stream are then mixed so that combustion can take place.

At a point downstream of the combustion preheat zone (e.g., the reaction zone), the hydrocarbon fuel stream and the oxidant stream can be mixed together to exothermically react to produce combustion products and heat. Preferably, the hydrocarbon fuel and oxidant components are mixed together in the mixing component within the pyrolysis reactor.

The combustion products are then flowed downstream to a combustion heat transfer zone (e.g., a portion of the first and/or second zone proximate to the thermal mass) with thermal mass located in the combustion heat transfer zone absorbing heat produced from the combustion of the combustion streams. This absorbed heat by the material in combustion heat transfer zone is sufficient to enable pyrolysis of the hydrocarbon stream (e.g., hydrocarbons in the pyrolysis feed) that flow through the pyrolysis preheat zone (e.g., a portion of the first and/or second zone of thermal mass) in the pyrolysis step, which is carried out in a flow direction that is the reverse of the flow direction of the combustion step. The combustion heat may also be sufficient to enable coke or tar components that may have accumulated in the combustion heat transfer zone during a previous pyrolysis step to be burned, thereby regenerating the combustion heat transfer zone. This heating and regeneration of the heating step is particularly beneficial in a cyclic process that incorporates both the heating step and the pyrolysis step.

IV. Pyrolysis Step of a Reverse Flow Reactor

In the pyrolysis step of a reverse-flow reactor, pyrolysis feed comprised of hydrocarbon, and optionally diluent, can be supplied to or injected into an end of the reactor via pyrolysis injection components. The pyrolysis feed may be supplied to or injected into the pyrolysis reactor following the removal of the combustion products from the heating step, which may include a sweeping or purging step to remove products from the internal regions of the entire reactor. That is, the pyrolysis stream can be configured to flow through the first and/or second end of the thermal mass of a reverse-flow reactor. In a reverse-flow reactor, the pyrolysis or hydrocarbon stream is typically provided at a different end of the reactor from the end that the combustion streams were supplied or injected. In other words, direction of flow of the pyrolysis stream may be counter to (e.g., reverse of) the direction of flow of the combustion streams, or in certain aspects may be in the same direction, which may also involve some alternating patterns of flow.

As the pyrolysis feed stream flows through the pyrolysis preheat zone, the temperature of the pyrolysis feed increases. As the temperature increases to the appropriate level, pyrolysis of the hydrocarbon in the pyrolysis feed stream takes place, typically in the reaction zone, as a result of heat transfer from the reactor's thermal mass. Following the reaction zone, the pyrolysis products (e.g., unreacted and reacted hydrocarbons) are flowed through a pyrolysis quenching zone, which reduces the temperature of the pyrolysis products such as below the peak pyrolysis temperature. Typically, pyrolysis products flowed through the same channels in the thermal mass as are used for conveying fuel and oxidant in the reverse-flow direction during a combustion step. The pyrolysis products can be removed from the pyrolysis quenching zone, and further passed for processing in recovery units to process and separate one or more of ethylene, acetylene and hydrogen.

In the pyrolysis step, the pyrolysis reaction is carried out relatively quickly to avoid over-cracking so as to avoid excessive formation of undesirable by-products, particularly coke and tar compositions. Accordingly, pyrolysis reactors may be characterized in terms of the residence time of total pyrolysis gases (e.g., feed and product gases) within the thermal mass of the pyrolysis reactor.

Different types of thermal pyrolysis reactors may have different heat profiles. That is, some embodiments of pyrolysis reactors may operate in an isothermal manner with the heat profile (i.e., peak pyrolysis temperature profile) being relatively constant. However, other pyrolysis reactors may have a peak pyrolysis temperature profile that is similar to a Gaussian curve. As an example, a regenerative reactor may be characterized by an initial and final temperature, as well as comprising a peak pyrolysis temperature profile over a specified temperature range.

The pyrolysis reactor typically includes a quenching zone in a portion of the thermal mass, especially in a portion of the reactor in which the endothermic reactions are slowed. That is, average temperature within the quenching zone is less than the peak pyrolysis temperature range of the reaction zone, such as at least 50° C. or at least 100° C. or at least 200° C. less than the peak pyrolysis temperature in the reaction zone.

In the quenching zone, the peak pyrolysis reaction temperature may be lowered (i.e., the reaction quenched) at desired ethylene conversion ratios by cooling the reaction gas or products to reduce further reactions that may form carbon and other less desired hydrocarbon compounds. The quenching is generally a rapid cooling that involves passing the pyrolysis products through or across the thermal mass. In certain embodiments, the quenching zone may be actively performed by injecting water, other hydrocarbons, oil, solvent or other suitable fluids into the reactor to substantially cool below the peak pyrolysis temperature.

As may be appreciated, the flow of pyrolysis feed can be interrupted after a desired or predetermined time and the combustion feed can be provided to again heat the reactor, such as in the reverse flow direction of the pyrolysis feed in a reverse-flow reactor. By repeating the heating step and the pyrolysis step, the overall reaction process can be continuously carried out over a relatively long period of time.

As an example of a reverse flow reaction, during a first time interval, a pyrolysis feed can be passed to a reactor such as a reverse-flow reactor comprising a thermal mass, with the thermal mass having a first zone, a second zone, and with the reaction zone being intermediate to the first and second zones. Heat from the first zone (which contains previously-heated thermal mass) can be transferred from the thermal mass to the pyrolysis feed, preferably exposing the pyrolysis feed to the desired peak pyrolysis temperature and hydrocarbon partial pressure conditions in the reaction zone, which produces pyrolysis product comprising desired levels of $C_2$ unsaturates. Heat from the pyrolysis product can be transferred to the second zone (which contains a previously cooled thermal mass) to cool the pyrolysis product to a temperature below the peak pyrolysis temperature, with the passing of the pyrolysis feed to the reverse-flow reactor being discontinued at the desired cooling level.

Optionally, during a second time interval, combustion feed can be provided to the reverse-flow reactor, with heat being transferred from the second zone to the combustion feed. The hydrocarbon fuel and oxidant components of the combustion feed can exothermically react to produce combustion products and heat. Heat from the combustion reaction can be transferred to thermal mass located proximate to the first zone of the reactor to cool the combustion products, with the passing of the combustion feed to the reverse-flow reactor being lessened or discontinued at the desired heating level.

V. Pyrolysis Conditions for Producing Ethylene

In the present invention, the pyrolysis reactor is operated so that the reaction zone of the reactor is at a peak pyrolysis temperature range effective for producing high quantities of ethylene from hydrocarbon in the pyrolysis feed as compared to typical pyrolysis reactions. In particular, the pyrolysis reactor is operated to expose a pyrolysis feedstock to a peak pyrolysis temperature of less than 1200° C. in the pyrolysis zone of the reactor. Alternatively, the pyrolysis reactor is operated to expose a pyrolysis feedstock to a peak pyrolysis temperature in the pyrolysis zone of the reactor in the range of from 850° C. to 1200° C., or from 850° C. to less than 1200° C., or from 900° C. to 1150° C., or from 900° C. to 1100° C.

In the present invention, the pyrolysis reactor is further operated at a pressure range effective for producing high quantities of ethylene from hydrocarbon in the feed relative to typical pyrolysis reactions. In particular, the pyrolysis reactor is operated to expose a pyrolysis feedstock to an effective ethylene-producing temperature within the pyrolysis zone at a pressure range further effective for producing high quantities of ethylene. For example, the pyrolysis reaction is highly effective at a pressure condition in which the hydrocarbon in the pyrolysis zone of the reactor has a partial pressure of ≥7 psia (48 kPa), or ≥10 psia (69 kPa), or ≥20 psia (138 kPa), or ≥30 psia (207 kPa).

The pyrolysis reaction can be effectively carried out to produce high quantities of ethylene over a wide range of pressures, including relatively high pressures. For example, the pyrolysis reaction is highly effective at a pressure condition in which the pyrolysis zone of the reactor is at a total pressure of ≥5 psig (34 kPag), or ≥15 psig (103 kPag), or ≥40 psig (276 kPag), or ≥80 psig (552 kPag), or ≥120 psig (827 kPag). For practical considerations on total pressure, the pyrolysis reaction can be carried out at a pressure condition in which the pyrolysis zone of the reactor is at a total pressure of ≤500 psig (3447 kPag), or ≤300 psig (2068 kPag), or ≤150 psig (1034 kPag).

Total gas residence time for the pyrolysis gas stream (i.e., total gas comprising the feed and product components) within the thermal mass of the pyrolysis reactor are relatively short. For example, pyrolysis feed can be passed through the thermal mass of the reactor at a total gas residence time in the thermal mass of ≤1.0 second, or ≤0.8 second; preferably ≤0.75 second or ≤0.6 second; or in the range of 0.001 second to 1.0 second, or in the range of 0.01 second to 0.8 second, or in the range of and 0.01 second to 0.75 second.

Total gas residence time for the pyrolysis gas stream passing through the thermal mass of the reactor is particularly short at higher temperatures in order to produce greater quantities of the desired $C_2$ unsaturates. Preferably, the pyrolysis reactor is configured so that pyrolysis feed can be passed through the thermal mass, encountering a temperature greater than 800° C. for only a relatively short residence time. For example, the pyrolysis feed can be passed through the thermal mass of the reactor at a total gas residence time above 800° C. in the thermal mass of ≤0.100 second, such as ≤0.060 second, such as ≤0.040 second, or in the range of 0.001 second to 0.100 second, or in the range of 0.002 second to 0.060 second, or in the range of and 0.002 second to 0.040 second.

For a regenerative reactor, the process may operate at cycle times in the range of 1 second to 240 seconds, in the range of 1 second to 60 seconds, in the range of 2 seconds to 40 seconds, in the range of 2 seconds to 20 seconds, or in the range of 3 seconds to 10 seconds.

A substantial amount of ethylene can be produced at the appropriate temperature, pressure and contact conditions as noted herein. For example, the pyrolysis feedstock can be exposed at the appropriate temperature, pressure and contact conditions to convert ≥10 wt %, or ≥20 wt %, or ≥30 wt %, or ≥40 wt %, or ≥50 wt % of total hydrocarbon in the feedstock to $C_2$ unsaturates. The $C_2$ unsaturates will have a relatively high concentration of ethylene compared to typical processes. For example, the $C_2$ unsaturates can have an ethylene:acetylene molar ratio of ≥1:1, ≥5:1, or ≥10:1, or ≥15:1.

VI. Pyrolysis Feed

A pyrolysis feed is injected into a first end of a pyrolysis reactor and flowed through a reaction zone within the pyrolysis reactor in which the reaction zone is at a process condition that pyrolyzes hydrocarbon in the feed to produce a pyrolyzed hydrocarbon product. Pyrolysis (alternatively pyrolysis process or pyrolyzation) is generally defined as a thermal decomposition process in which the pyrolysis feed is heated, generally in the absence of oxidative combustion, to decompose hydrocarbon (i.e., break or crack the C—C and/or C—H bonds of the hydrocarbon) to produce unsaturated hydrocarbon molecules.

In general, pyrolysis feed refers to a hydrocarbon-containing feed that is fed to (i.e., enters) the pyrolysis reactor for conversion into pyrolysis products including $C_2$ unsaturates. The hydrocarbon in the pyrolysis feed can be derived from any hydrocarbon feed capable of being thermally cracked into unsaturated hydrocarbon compounds. The hydrocarbon may be optionally treated for use as pyrolysis feed, or a component thereof. For example, hydrocarbon can include substantial amounts of non-volatiles such that the hydrocarbon itself would not be desirable as a pyrolysis feed component, unless at least a portion of the non-volatiles was removed. In such cases, the hydrocarbon can be treated to lessen the amount of non-volatiles, or any other type of hydrocarbon or non-hydrocarbon component as desired. Examples of such treatment include, but are not limited to, treatment by resid hydrotreaters, hydrovisbreakers, acid washes, filtration, chelation, membrane or filtration, distillation, solvent extraction, adsorption, resid hydrotreater, acid extraction, or any number of metals reduction processes.

Hydrocarbons useful as pyrolysis feed or components of a pyrolysis feed include chemical compounds having at least one C bound to at least one H. The hydrocarbon compounds may contain (i) minor components of covalently bound heteroatoms (less than (<) 10 weight percent (wt %)) and (ii) minor components of non-covalently bound heteroatoms (<10 wt %) (e.g., $H_2O$), wherein these weight percentages are based on total weight of the hydrocarbon feed. Reference to "hydrocarbon compounds" or "hydrocarbons in the pyrolysis feed" means molecules that contain at least hydrogen and carbon and, optionally containing one or more heteroatoms such as oxygen, sulfur and nitrogen. Weight percentages of hydrogen and carbon, as used to characterize the hydrocarbon content of the pyrolysis feed, are typically provided as a percentage of the total hydrocarbon compounds in the pyrolysis feed. Preferably, the hydrocarbon compounds are comprised of at least 75 percent (%) of both carbon and hydrogen, based on total atom content of the hydrocarbon compounds in the total pyrolysis feed to the reactor.

The hydrocarbon portion of the pyrolysis feed may include, by way of non-limiting examples, one or more of ethane and $C_{3+}$ hydrocarbons, in which $C_{3+}$ hydrocarbons refers to compounds containing three or more carbon atoms. For example, the hydrocarbon of the pyrolysis feed can comprise one or more of propane, propylene, butane, butylene and higher hydrocarbons. Additional examples of $C_{3+}$ hydrocarbons include, but are not limited to Fischer-Tropsch products, shale gas, biogas, associated gas, natural gas and mixtures or components thereof, steam cracked gas oil and residues, gas oils, heating oil, jet fuel, diesel, kerosene, gasoline, naphtha (including coker naphtha, steam cracked naphtha, and catalytically cracked naphtha), hydrocrackate, reformate, raffinate reformate, Fischer-Tropsch liquids, natural gasoline, distillate, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, $C_4$'s/residue admixture, naphtha residue admixture, cracked feed, coker distillate streams, hydrocarbon streams derived from plant or animal matter and any mixtures thereof.

Particular hydrocarbons useful in pyrolysis feed according to this invention are those that can be pyrolyzed to produce a product containing alkene compounds, particularly ethylene, at the desired pyrolysis conditions of temperature, pressure and total gas residence times. Typically, the hydrocarbon compounds are those that can be pyrolyzed to produce product containing equal to or greater than ($\geq$) 1 volume percent (vol. %), more preferably $\geq$3 vol. %, and most preferably $\geq$6 vol. % alkene compounds (particularly ethylene), based on total volume of pyrolyzed product produced form the pyrolysis process.

In an embodiment, the pyrolysis feed or feed mixture can comprise hydrocarbon rich in ethane in which $\geq$10 wt %, or $\geq$20 wt %, or $\geq$30 wt %, or $\geq$40 wt %, or $\geq$50 wt % of total hydrocarbon in the feedstock is converted to $C_2$ unsaturates. For example, hydrocarbon rich in ethane can be hydrocarbon comprised of $\geq$50 wt %, or $\geq$60 wt %, or $\geq$70 wt %, or $\geq$80 wt %, or $\geq$90 wt % ethane. The ethane can be provided from any source. For example, the ethane can be provided from synthetic or natural sources. In one embodiment, the ethane is provided from a petroleum refining process. In an alternative embodiment, the ethane is provided from a geological source or geological origin, such as natural gas.

The pyrolysis feed optionally includes one or more diluents. Typical diluents are compounds that are essentially non-reactive under pyrolysis conditions as specified herein, e.g., compounds that are essentially resistant to cracking at the pyrolysis conditions in the pyrolysis zone of the reactor. Diluent can be used to moderate the pyrolysis reaction, e.g., to control total pressure in the reactor. Examples of useful diluents include, but are not limited to, one or more of methane, water (e.g., steam), hydrogen, nitrogen and the noble gases, such as helium, neon and argon.

In an embodiment, the pyrolysis feed or feed mixture can comprise diluent in which $\geq$10 wt %, or $\geq$20 wt %, or $\geq$30 wt %, or $\geq$40 wt %, or $\geq$50 wt % of total pyrolysis feed or first mixture is diluent. The amount of diluent typically depends on desired total pressure of the pyrolysis reaction carried out in the reaction zone and desired partial pressure of the hydrocarbon. Diluent is particularly useful to increase total pressure and to reduce coke formation. For example, diluent can be particularly useful at a total pyrolysis pressure of $\geq$15 psig (103 kPag), or $\geq$40 psig (276 kPag), or $\geq$80 psig (552 kPag), or $\geq$120 psig (827 kPag).

In certain aspects, the diluent comprises at least one of methane and water. In an embodiment the pyrolysis feed can be comprised of a natural gas such as a shale gas that comprises a majority of methane and a minority of ethane and $C_{3+}$ hydrocarbons. In such an embodiment, the diluent can be comprised of at least one of methane and water in an amount of $\geq$50 wt %, or $\geq$60 wt %, or $\geq$70 wt %, or $\geq$80 wt %, or $\geq$90 wt % of the total diluent in the pyrolysis feed or first mixture. Such diluents are particularly useful at the total pressures previously indicated.

The pyrolysis feed can comprise a volatile hydrocarbon component and a non-volatile hydrocarbon component. A volatile hydrocarbon may be referred to as a hydrocarbon that can be vaporized at one atmosphere, with little if any residue remaining after achieving final boiling point. Volatile hydrocarbons useful according to the present invention can include lower boiling point hydrocarbons. For example, the volatile hydrocarbon component may be a hydrocarbon composition having a final boiling point of not greater than 1050° F. (566° C.), which can also be referred to as a 1050° F.$^-$ (566° C.$^-$) fraction. Boiling points as referred to herein are preferably determined according to ASTM D86-07 Standard Test Method for Distillation of Petroleum Products at Atmospheric Pressure.

A non-volatile hydrocarbon component may be referred to as a composition that cannot be vaporized at one atmosphere or cannot be adequately vaporized without substantial deposit of solid or semisolid residue. The non-volatile component, i.e., "non-volatiles," can be more particularly defined by asphaltene content. Asphaltenes are semisolids or solids, which can be determined according to ASTM D6560-00 (2005) Standard Test Method for Determination of Asphaltenes (Heptane Insolubles) in Crude Petroleum and Petroleum Products. Asphaltenes can be found in heavy hydrocarbon fractions. For example, asphaltenes can be found in 1050° F.+(566° C.+) fractions (hydrocarbons that have a boiling point of at or above 1050° F. (566° C.). As a further example, Arab Medium crude contains about 25 wt. % vacuum resid (a 1050° F.+(566° C.+) fraction). Vacuum resid has an asphaltene content of about 12 wt % and a non-combustible non-volatile (ash) content of as low as 150 ppmw.

The non-volatile hydrocarbon component can comprise a mixture of combustible non-volatiles (combustible non-volatile component) and non-combustible non-volatiles (non-combustible non-volatile component). The non-combustible, non-volatile content can be determined according to ASTM D482-07 Standard Test Method for Ash from Petroleum Products. The combustible non-volatile content can, therefore, be determined as the non-volatile component (asphaltene) content minus the non-combustible non-volatile content.

VII. Pyrolysis Product

The pyrolysis product, also referred to herein as a product mixture, is the effluent mixture from the pyrolysis reaction zone. The pyrolysis product typically comprises $C_2$ unsaturates (ethylene and/or acetylene), unreacted pyrolysis feed, $C_{3+}$ hydrocarbon, non-volatiles, etc.

The pyrolysis product typically has a relatively high molar ratio of alkene to alkyne (e.g., ethylene to acetylene). For example, the pyrolysis product can be comprised of ethylene and acetylene at a respective molar ratio of $\geq 2:1$, or $\geq 5:1$, or $\geq 10:1$.

The pyrolysis product can include non-alkyne and non-alkene compounds, as well as any unreacted hydrocarbon feed and diluent, typically in relatively small amounts. For example, the pyrolysis product can include $\leq 30$ wt % non-alkyne and non-alkene compounds, including unreacted hydrocarbon and diluent, alternatively $\leq 40$ wt % non-alkyne and non-alkene compounds, including unreacted hydrocarbon and diluent, or $\leq 50$ wt % non-alkyne and non-alkene compounds, including unreacted hydrocarbon and diluent, based on total weight of the pyrolysis product as it emerges from the pyrolysis reactor. In a particular aspect, the diluent comprises methane and the pyrolysis product includes >70% non-alkyne and non-alkene compounds, including unreacted hydrocarbon and diluent, based on total weight of the pyrolysis product.

VIII. $C_2$ Unsaturates Recovery

Gaseous effluent is withdrawn from the pyrolysis product, and the $C_2$ unsaturates are separated for additional processing or upgrading into derivative products. Ethylene is a particularly desired pyrolysis product, and it is advantageous to recover the ethylene in a highly pure form for additional processing or upgrading into derivative products.

The recovery of $C_2$ unsaturates, particularly ethylene, from pyrolysis processes typically involves compressing the gaseous effluent to much higher pressures in order to enhance the ability of effectively separate the desired $C_2$ unsaturates. Since the pyrolysis process of this invention produces relatively large quantities of $C_2$ unsaturates at relatively high pressures, recovery of the $C_2$ unsaturates, particularly ethylene, can be accomplished at a substantial reduction in compression energy.

In certain aspects, the $C_2$ unsaturates, such as ethylene, can be separated from the pyrolysis product, which emerges from or exits the pyrolysis reactor, without increasing total pressure of the pyrolysis product exiting the pyrolysis reactor. In other aspects, the $C_2$ unsaturates, such as ethylene, can be separated from pyrolysis product, which emerges from or exits the pyrolysis reactor, by increasing total pressure of the pyrolysis product exiting the pyrolysis reactor by a factor of $\leq 2.0$, or $\leq 5.0$, or $\leq 10.0$.

A recovery system can be used for separating $C_2$ unsaturates from the gaseous effluent or compressed gaseous effluent. Such recovery systems generally comprise one or more or a combination of a various separation, fractionation and/or distillation towers, columns, splitters, or trains, and other associated equipment for example various condensers, heat exchangers, refrigeration systems or chill trains, compressors, knock-out drums or pots, pumps, and the like.

Non-limiting examples of separation towers, columns, splitters or trains, which used alone or in combination, include one or more of a demethanizer, preferably a high temperature demethanizer, a dethanizer, a wash tower (often referred to as a caustic wash tower and/or quench tower), absorbers, adsorbers, membranes, ethylene ($C_2$) splitter, propylene ($C_3$) splitter, and the like.

Various recovery systems useful for recovering predominately olefin(s), preferably prime or light olefin(s) such as the $C_2$ unsaturates, as well as propylene and/or butylene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, byproducts and/or contaminants along with the preferred prime products. The preferred prime products, the $C_2$ unsaturates, such as ethylene and acetylene, particularly ethylene, are typically purified for use in derivative manufacturing processes such as polymerization. The recovery system, therefore, generally also includes a purification system that removes low levels of byproducts or contaminants.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249-271 and 894-899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. Pat. No. 6,593,506.

IX. Derivative Products

The $C_2$ unsaturates produced according to this invention can be polymerized to form derivative products, particularly plastic compositions, e.g., polyolefins, particularly polyethylene. Any process for forming polyethylene can be used. Catalytic processes are preferred. Particularly preferred are metallocene, Ziegler/Natta, chromium oxide and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the ethylene product with a polyolefin-forming catalyst at a pressure and temperature effective to form the polyolefin product.

In one embodiment of this invention, the ethylene product is contacted with a metallocene catalyst to form a polyolefin. Desirably, the polyolefin forming process is carried out at a temperature ranging between about 50° C. and about 320° C.

The reaction can be carried out at low, medium or high pressure, being anywhere within the range of about 1 bar absolute ("bara") to about 3200 bara. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives can be formed from the olefin products produced according to this invention. The olefins produced according to this invention can also be used in the manufacture of such compounds as aldehydes, acids such as $C_2$-$C_{13}$ mono carboxylic acids, alcohols such as $C_2$-$C_{12}$ mono alcohols, esters made from the $C_2$-$C_{12}$ mono carboxylic acids and the $C_2$-$C_{12}$ mono alcohols, linear alpha olefins, vinyl acetate, ethylene dichloride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene.

X. Examples

Example 1

The pyrolysis reaction of this invention can carried out in any reactor capable of temperature, pressure and contact time constraints for producing high quantities of ethylene from hydrocarbon in the pyrolysis feed. In an embodiment, the pyrolysis reactor is a regenerative reactor system such as a regenerative, reverse-flow reactor system.

Figure 1A:
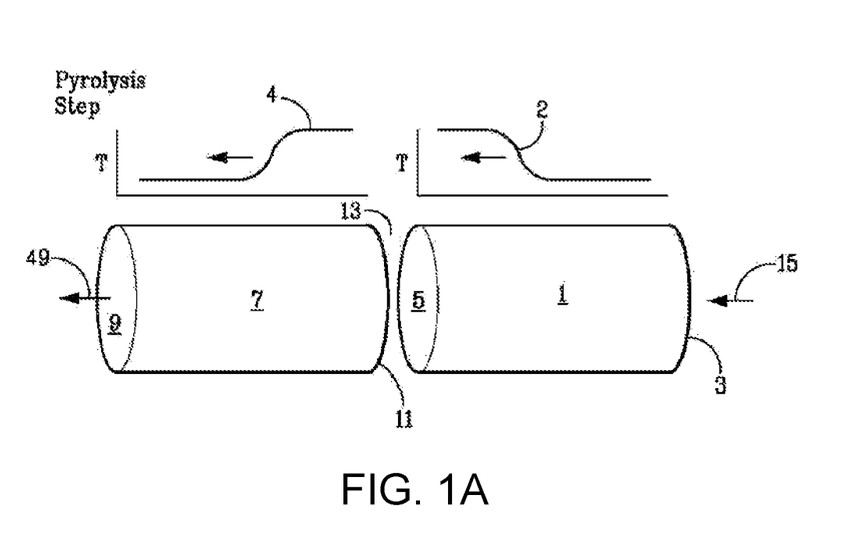
FIGS. 1A &1B are a schematic representation of a two-step asymmetric cycle of a regenerative bed reactor system, which can be in carrying out the techniques of this invention.
Figure 1B:
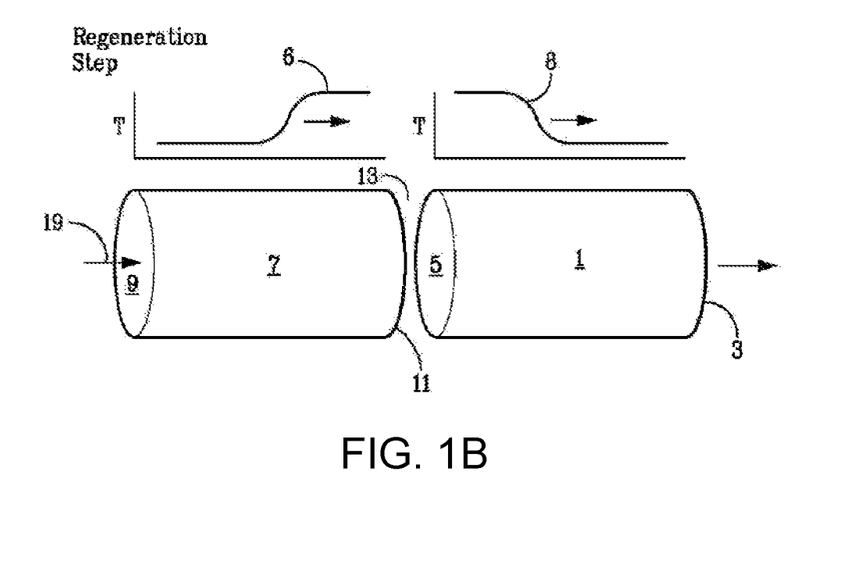

A basic two-step asymmetric cycle of a regenerative bed reactor system is depicted in FIGS. 1A and 1B. The regenerative bed reactor system is shown as a reactor system having separate thermal mass zones, including a second zone (7) [which includes a recuperator/quenching zone toward a first end (9), as well as a portion of a reaction or pyrolysis zone proximate to a second end (11) of the second zone (7)] and a first zone (1) [also including a portion of the reaction or pyrolysis zone proximate to secondary end (5) of the first zone (1)]. Both the first zone (1) and the second zone (7) contain regenerative beds comprising thermal mass. The term regenerative reactor means a regenerative media that may also be used for carrying out a chemical reaction. The thermal mass may comprise material that is effective in storing and transferring heat, such as glass or ceramic beads or spheres, metal beads or spheres, ceramic (including zirconia) or metal honeycomb materials, ceramic tubes, extruded monoliths, and the like, provided they are competent to maintain integrity, functionality, and withstand long term exposure to temperatures in excess of the desired pyrolysis temperatures, e.g., 1200° C. (2192° F.) for safe operating margin.

As shown in FIG. 1A, at the beginning of the "pyrolysis step" of the reverse flow cycle, a secondary end (5) of the first zone (1) of the reactor is at an elevated temperature as compared to the primary end (3) of the first zone (1), and at least a portion of the second zone (7) [e.g., the first end (9) of the second zone (7)] is at a lower temperature than the reaction zone [i.e., the portion between the secondary end (5) of the first zone (1) and the second end (11) of the second zone (7)] to provide a quenching effect for the reaction product. A hydrocarbon-containing pyrolysis feed, optionally comprising a diluent such as methane or steam, is introduced via at least one conduit (15) into the primary end (3) of the first zone (1).

The pyrolysis feed absorbs heat from the first zone (1), and the hydrocarbon of the pyrolysis feed is endothermically reacted to produce the desired $C_2$ unsaturates. As this step proceeds, a shift in the temperature profile (2), as indicated by the arrow, is created based on the heat transfer properties of the system. The thermal mass has heat transfer capability configured to provide a relatively sharp temperature gradient, which gradient will move across the first zone (1) as the endothermic reaction step proceeds. The sharper the temperature gradient profile, the better the reaction may be controlled. As the pyrolysis stream transits the reactor it is first heated and then cooled. At some point of maximum temperature, it will achieve its peak pyrolysis temperature. The reaction or pyrolysis zone is considered to be the location proximate to (e.g., at, near, within, or on) the reactor's thermal mass where the pyrolysis process is carried out at a temperature above 800° C., and the pyrolysis feed is exposed to this zone for a short residence time.

Pyrolysis reaction gas (gas undergoing the pyrolysis reaction) exits the zone (1) through a secondary end (5) at an elevated peak pyrolysis temperature and passes through the zone (7), entering through a second end (11), and exiting at a first end (9) as a pyrolysis product comprising ethylene, acetylene, some unconverted hydrocarbon and diluent, as well as other reaction products. As the pyrolysis reaction gas passes through the zone (7), heat is transferred to the thermal mass in the zone (7), and hot pyrolysis product is quenched or cooled to a temperature below the peak pyrolysis temperature. For example, the temperature of the cooled pyrolysis product can approach the temperature substantially at the first end (9). As the pyrolysis reaction gas is cooled in the zone (7), a temperature gradient (4) representative of peak pyrolysis temperature is created in the zone's regenerative bed(s) and moves across the zone (7) during the pyrolysis reaction. After quenching, the pyrolysis product exits the zone (7) at (9) and is conducted away from the pyrolysis reactor. The pyrolysis product can be processed for separation and recovery of the various components, e.g., ethylene.

The second step of the cycle (FIG. 1B), referred to as the "regeneration step" of the reverse flow cycle, includes a step of introducing combustion feed into the reactor in the reverse flow direction relative to the flow of the pyrolysis feed. For example, the hydrocarbon fuel and oxidant components of the combustion feed can be introduced via separated conduits or channels (19) within, for example, a thermal mass material. The thermal mass material can be in the form of a honeycomb comprising at least one first channel and one second channel separated by a barrier, which that prevents at least a majority of a stoichiometrically reactable amount of the hydrocarbon fuel from reacting with the oxidant within the zone (7). Separate streams of hydrocarbon fuel and oxidant can pass separately through hot zone (7) toward the second end (11) of the zone (7), where the separate streams are combined for exothermic reaction or combustion in or near the reaction zone (13) of the reactor system. In doing so, the temperature gradients (6) and (8) may move across the beds as illustrated by the arrows on the exemplary graphs in FIG. 1B, similar to, but in opposite directions of, the graphs of the temperature gradients carried out during the reaction cycle in FIG. 1A. The heat recovered from the zone (7) together with the heat of combustion is transferred to the reaction zone (13), thermally regenerating the thermal mass of the reaction zone.

Example 2

Figure 2:
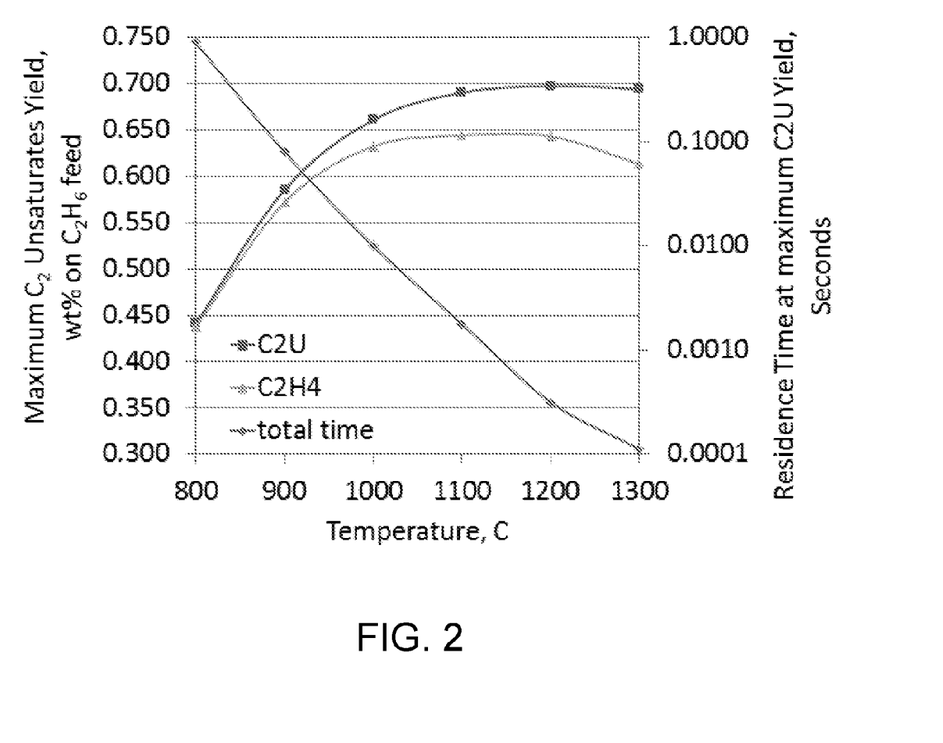
FIG. 2 shows a model prediction for maximum $C_2$-unsaturate (ethylene+acetylene) yield from ethane cracking at specified cracking temperatures and cracking times.

The impact of temperature and residence time at pyrolysis temperature on $C_2$ unsaturates production is shown in FIG. 2. The data shown in FIG. 2 are based on a model prediction for maximum $C_2$ unsaturates (ethylene+acetylene) yield from hydrocarbon cracking at the indicated cracking temperatures, along with the cracking time needed at the given temperatures. The model used for this Example can be carried out as described by Chen Xu et al., Kinetic Modeling of Ethane Pyrolysis at High Conversion, *J. Phys. Chem. A* 2011, 115, 10470-10490, which is fully incorporated herein by reference.

The cases shown in FIG. 2 represent cracking of ethane-containing pyrolysis feed (with the pyrolysis feed comprising 33 mole % steam) at 35 psia (2.4 bara) (initial ethane partial pressure of 23 psia) (1.6 bara). The maximum $C_2$ unsaturates ($C_2U$=ethylene+acetylene) and ethylene ($C_2H_4$) yields from the cracking runs are plotted against the cracking temperature.

FIG. 2 shows that below 900° C., the maximum $C_2$ unsaturates and ethylene yields are below 60 weight percent. By raising temperature to 1100° C., the maximum yields can be increased to almost 70% for $C_2$ unsaturates, with almost 65% of the yield being ethylene. Very little additional $C_2$ unsaturates and ethylene yields are achieved at temperatures above 1100° C. FIG. 2 further shows that as temperature is increased, ethylene yield begins to decrease at around 1200° C.

FIG. 2 further demonstrates the impact of residence time at pyrolysis temperature. Residence times of several hundred milliseconds are needed to achieve maximum $C_2$ unsaturates and ethylene yields at temperatures below 900° C. At temperatures above 900° C., residence times needed to achieve maximum $C_2$ unsaturates and ethylene yields are significantly reduced. Since the residence times at high pyrolysis temperatures are significantly reduced, reactor productivity can be significantly increased.

Example 3

Figure 3:
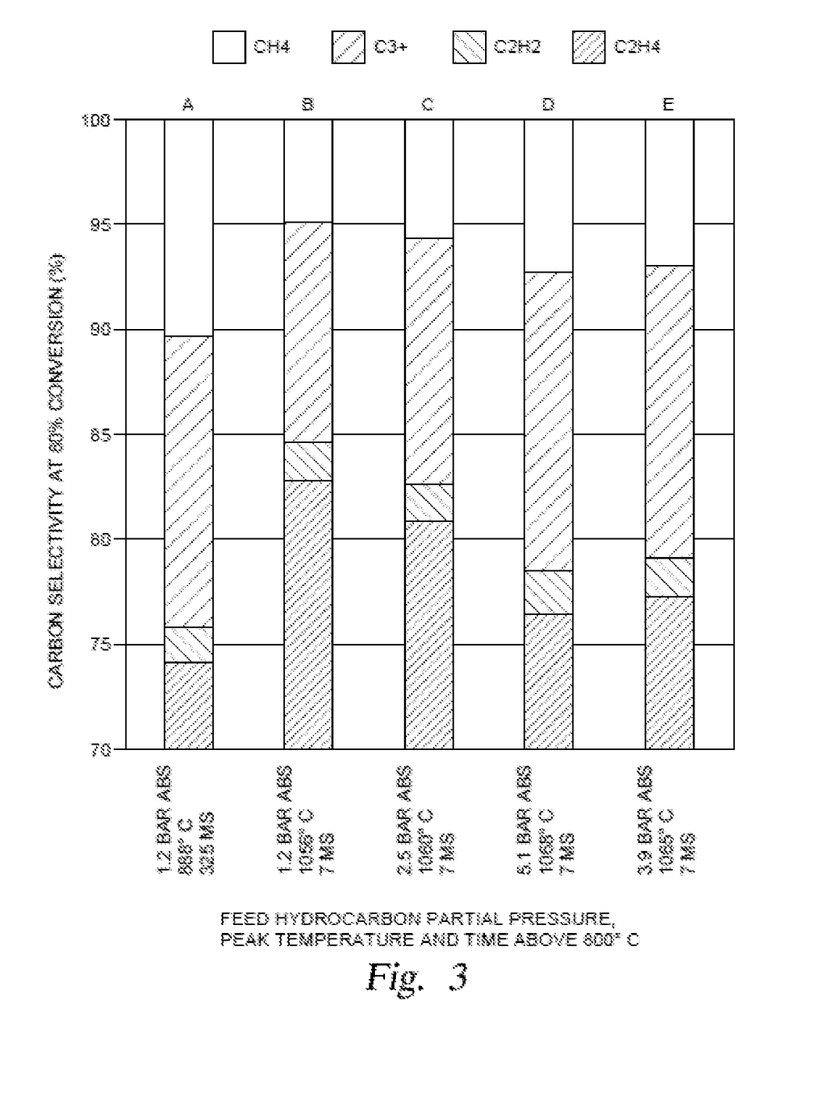
FIG. 3 is a comparison of four aspects of the invention against a conventional steam cracking profile.

FIG. 3 compares four different predictive runs of pyrolysis processes representative of the invention (Bars B-E) against a conventional steam cracking process (Bar A), with the predictive model being the same as that described in Example 2. All reactions are run at 80% conversion. Total pressure for each run shown in FIG. 3 is as follows: A=21 psig (1.43 barg); B=22 psig (1.5 barg); C=22 psig (1.5 barg); D=60 psig (4.1 barg); E=100 psig (6.8 barg). Partial pressure of the hydrocarbon in each pyrolysis feed stream is shown for each run in FIG. 3. Peak pyrolysis temperature and the total residence time at temperature above 800° C. are also shown in FIG. 3. In runs A, B and E, diluent (water) was included with the pyrolysis feed. Thus, in runs A, B and E, total pressure is equal to the sum of the partial pressures of the hydrocarbon and the water (steam) in the reactor. In cases C and D, no diluent was included with the pyrolysis feed. Thus, in cases C and D, total pressure equals hydrocarbon partial pressure.

As seen in FIG. 3, each of the runs representative of the invention (B-E) have a relatively high $C_2$ unsaturates selectivity ($C_2H_2+C_2H_4$), i.e., at least 79%, compared to about 76% for the comparative run (A). The B-E runs have $C_2$ unsaturates selectivities that are a substantial improvement over the comparative run.

The data in FIG. 3 reveals three modes in which the pyrolysis process carried out according to the invention add value to hydrocarbon cracking by:

(1) Operation with "normal" diluent (e.g., steam) and pressure levels to achieve substantially higher selectivity to ethylene;

(2) Operation at much higher pressure (with diluent) to avoid cost of compression for effective recovery of the $C_2$ unsaturates (e.g., ethylene) in the reaction product; and (3) Operation at moderate pressures without steam or other diluent to save diluent costs.

The principles and modes of operation of the invention have been described above with reference to various exemplary and preferred embodiments. As understood by those of skill in the art, the process, as defined by the claims, encompasses other preferred embodiments not specifically enumerated herein.

The invention claimed is:

1. A tubular, regenerative, reverse-flow thermal reactor for pyrolyzing hydrocarbon, the reactor comprising:
   (a) first and second zones, and a reaction zone located between the first and second zones,
   (b) first and second thermal masses, at least a portion of the first thermal mass being located in the first zone, and at least a portion of the second thermal mass being located in the second zone,
   (c) at least one combustion feed conduit comprising a fuel channel and a separate oxidant channel, the feed conduit being adapted for introducing a combustion feed comprising a fuel and an oxidant into the reactor proximate to the first zone and conveying the combustion feed to the reaction zone, wherein the fuel and oxidant channels are located within the portion of the first thermal mass that is located in the first zone,
   (d) at least one pyrolysis feed conduit for introducing a pyrolysis feed into the reactor proximate to the second zone and conveying pyrolysis feed to the reaction zone, and
   (e) one or more valves for (i) establishing during a first time interval a flow of the combustion feed in a forward direction through the first zone to the reaction zone for combustion and (ii) establishing during a second time interval a flow of the pyrolysis feed in a reverse direction through the second zone to the reaction zone for the pyrolysis, wherein
      the first zone is configured to transfer heat from the first thermal mass to the fuel and to the oxidant during the first time interval and to transfer heat from pyrolysis products to the first thermal mass during the second time interval,
      the reaction zone is configured to combust the combustion feed during the first interval and to expose the pyrolysis feed to a peak pyrolysis temperature in the range of from 850° C. to 1200° C., at a hydrocarbon pressure ≥7 psia (0.48 bara), for a residence time ≤1.0 seconds during the second time interval, and
      the second zone is configured to transfer heat from combustion products to the second thermal mass during the first time interval and to transfer heat from the second thermal mass to the pyrolysis feed during the second time interval.

2. The reactor of claim 1, wherein the first time interval and the second time interval are included in a cycle time, the cycle time being in the range of from 1 second to 240 seconds.

3. The reactor of claim 1, wherein the first time interval and the second time interval are included in a cycle time, the cycle time being in the range of from 1 second to 60 seconds.

4. The reactor of claim 1, wherein at least one of the first and second thermal masses has a melting point of at least 1500° C.

5. The reactor of claim 1, wherein at least one of the first and second thermal masses has a geometric void in the range of from 10% to 70%.

6. The reactor of claim 1, wherein at least one of the first and second thermal masses has a pore volume within a geometric solid, the pore volume being not greater than 20%.

7. The reactor of claim 1, wherein at least one of the first and second thermal masses has a bulk density in the range of from 0.5 g/cm$^3$ to 5 g/cm$^3$.

8. The reactor of claim 1, wherein at least one of the first and second thermal masses has a thermal conductivity in the range of from 0.1 W/mK to 50 W/mK.

9. The reactor of claim 1, wherein at least one of the first and second thermal masses has a thermal expansion coefficient in the range of from $0.2 \times 10^{-6}$/K to $15 \times 10^{-6}$/K.

10. The reactor of claim 1, wherein at least one of the first and second thermal masses has a thermal capacity in the range of from 500 J/dm$^3$K to 3000 J/dm$^3$K.

11. The reactor of claim 1, wherein at least one of the first and second thermal masses includes at least one ceramic selected from the group consisting of yttria, zirconia, alumina, and mixtures thereof.

12. The reactor of claim 1, wherein at least one of the first and second thermal masses has an average wetted surface area per unit volume in the range of about 5 cm$^{-1}$ to 50 cm$^{-1}$.

13. The reactor of claim 1, wherein at least one of the first and second thermal masses has a ceramic honeycomb monolith form.

* * * * *